United States Patent [19]
Baker et al.

[11] Patent Number: 5,569,251
[45] Date of Patent: Oct. 29, 1996

[54] IMPLANT DEVICE AND METHOD OF INSTALLING

[75] Inventors: Gregg S. Baker, Lake Forest; Paul B. Hafeli, El Toro, both of Calif.

[73] Assignee: BHC Engineering, L.P., Maitland, Fla.

[21] Appl. No.: 345,358

[22] Filed: Nov. 18, 1994

Related U.S. Application Data

[63] Continuation of Ser. No. 92,697, Jul. 16, 1993, abandoned.

[51] Int. Cl.⁶ ................................................. A61B 17/80
[52] U.S. Cl. ................................................. 606/69; 606/73
[58] Field of Search ............................ 606/60, 61, 69, 606/72, 73, 104, 105

[56] References Cited

U.S. PATENT DOCUMENTS

| | | | |
|---|---|---|---|
| 4,013,071 | 3/1977 | Rosenberg | 606/73 |
| 4,503,848 | 3/1985 | Caspar et al. | 606/69 |
| 4,611,581 | 9/1986 | Steffee . | |
| 4,716,893 | 1/1988 | Fischer et al. | 606/73 |
| 5,100,405 | 3/1992 | McLaren | 606/73 |
| 5,196,016 | 3/1993 | Buser et al. | 606/72 |
| 5,360,450 | 11/1994 | Giannini | 623/16 |

FOREIGN PATENT DOCUMENTS

| | | | |
|---|---|---|---|
| 504103 | 9/1992 | European Pat. Off. | 606/73 |
| 3601865 | 1/1987 | Germany | 606/73 |

OTHER PUBLICATIONS

"Cervical Spine Locking Plate," Synthes Spine, no date, 7 pages.
"Caspar Anterior Cervical Fusion Instrumentation and Trapezial Osteosynthetic Plates," AESCULAP, no date, 3 pages.

*Primary Examiner*—Michael Powell Buiz
*Assistant Examiner*—Guy V. Tucker
*Attorney, Agent, or Firm*—Finnegan, Henderson, Farabow, Garrett & Dunner, L.L.P.

[57] ABSTRACT

A component is an anchor having a hollow shank with an outer threaded surface for securely fixing to a bone and a threaded interior surface for cooperatively receiving a screw. The anchor cooperates with the screw that engages the interior surface of the shank to form an assembly for holding an element in place to support and strengthen the bone. A method for using the device includes forming a cavity in the bone; fixing the anchor; placing the element over the anchor; and fixedly attaching the plate by engaging the screw through the element and into the anchor.

29 Claims, 1 Drawing Sheet

IMPLANT DEVICE AND METHOD OF INSTALLING

This application is a continuation of application Ser. No. 08/092,697, filed Jul. 16, 1993, now abandoned.

BACKGROUND OF THE INVENTION

The present invention relates to an implant device and more particularly to an anchor for engaging a bone and for receiving a holding member.

Structural implants must attach to bone. Permanent joint replacements, known as arthroplasty devices, are cemented to bone or provided with an ingrowth surface for the bone to attach. However, bone cement tends to weaken and crack over time. Temporary fixation devices, such as plates or other structural elements, attach to the bone with a screw or similar simple mechanism. Screws tend to loosen in the bone, require precise alignment relative to the assembly, and inherently lack rigidity in an assembly consisting only of a plate and screws. Additionally, screw pullout strength is limited by the size of the screw outer diameter which fits through a corresponding hole in the structural element.

In light of the foregoing, there is a need for an implant device that supports and reinforces bone with improved rigidity, increased pullout strength, and reduced alignment requirements over the related art.

SUMMARY OF THE INVENTION

Accordingly, the present invention is directed to an assembly that substantially obviates one or more of the problems due to limitations and disadvantages of the related art.

The principal advantage of the present invention is the increased pullout strength and improved rigidity over the described prior arrangements.

Additional features and advantages of the invention will be set forth in the description which follows, and in part will be apparent from the description, or may be learned by practice of the invention. The objectives and other advantages of the invention will be realized and attained by the implant device particularly pointed out in the written description and claims hereof as well as the appended drawings.

To achieve these and other advantages and in accordance with the purpose of the invention, as embodied and broadly described, the invention includes an anchor having a hollow shank with an outer surface for engaging a bone and an interior surface. Means for engaging the interior surface of the anchor holds an element or plate between the engaging means and the anchor. The engaging means and the anchor have means for cooperating to fixedly attach the engaging means and the anchor together.

In another aspect, the invention includes at least one anchor having a hollow shank with an outer surface for engaging a bone and an interior surface. Additionally, the invention includes an element for fixing to a bone surface. Means for securing the element to each anchor engages the interior surface of each anchor.

In yet another aspect, the invention includes a method for attaching a plate having an opening to opposite sides of a fracture in a bone. A cavity is formed in the bone for receiving an anchor. The anchor having a hollow shank with an outer surface and an interior surface is fixed into the cavity. The plate is placed against the bone with the opening in the plate over the hollow shank of the anchor. The plate is fixedly attached by engaging a holding member into the hollow shank of the anchor, whereby the plate is held between the anchor and the holding member.

The assembly provides a more rigid structure that will not loosen over time compared to available related art. The present invention not only requires less precise alignment characteristics than related art, but also provides greater pullout strength through the use of an anchor having an outer diameter and external threads at the bone-implant interface limited in size only by the bone itself. The anchor provides a foundation for receiving or attaching anything from plates and rods to arthroplasty devices and artificial ligaments.

It is to be understood that both the foregoing general description and the following detailed description are exemplary and explanatory only and are not restrictive of the invention, as claimed.

BRIEF DESCRIPTION OF THE DRAWINGS

The accompanying drawings are included to provide a further understanding of the invention and are incorporated in and constitute a part of this specification, illustrate one embodiment of the invention and together with the description, serve to explain the principles of the invention.

IN THE DRAWINGS

Figure 1:
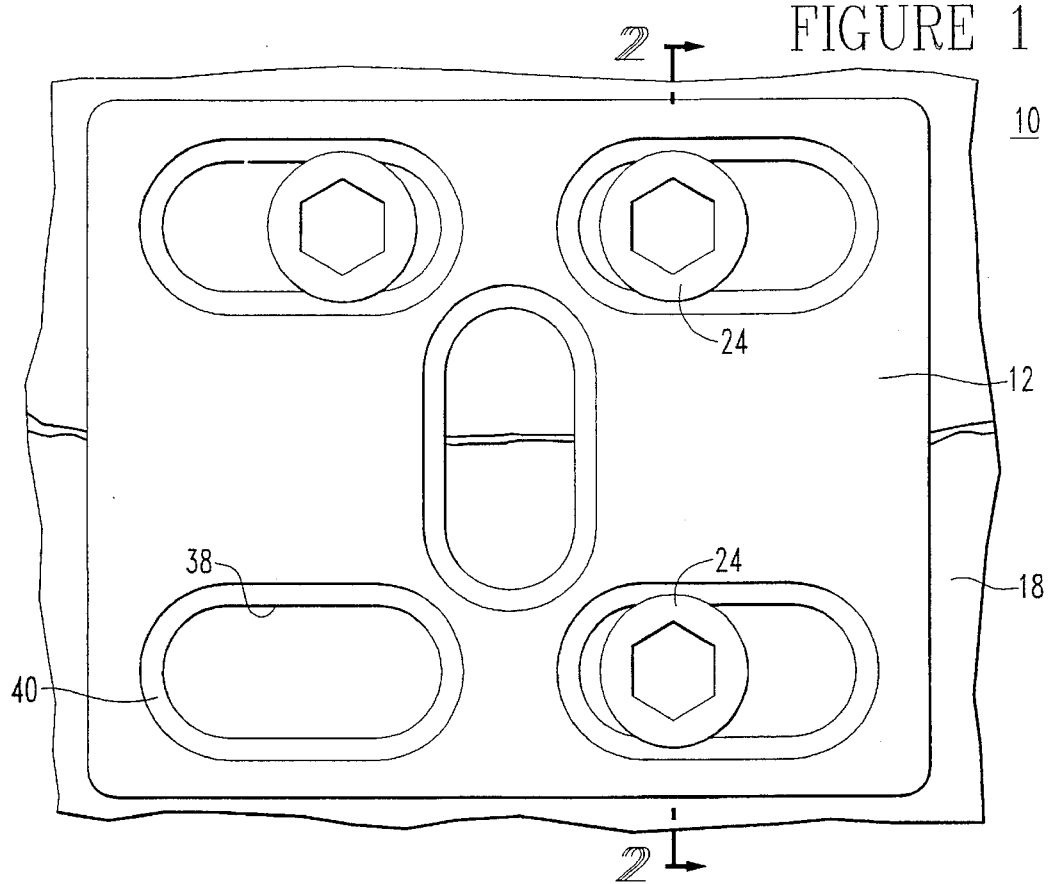
Figure 2:
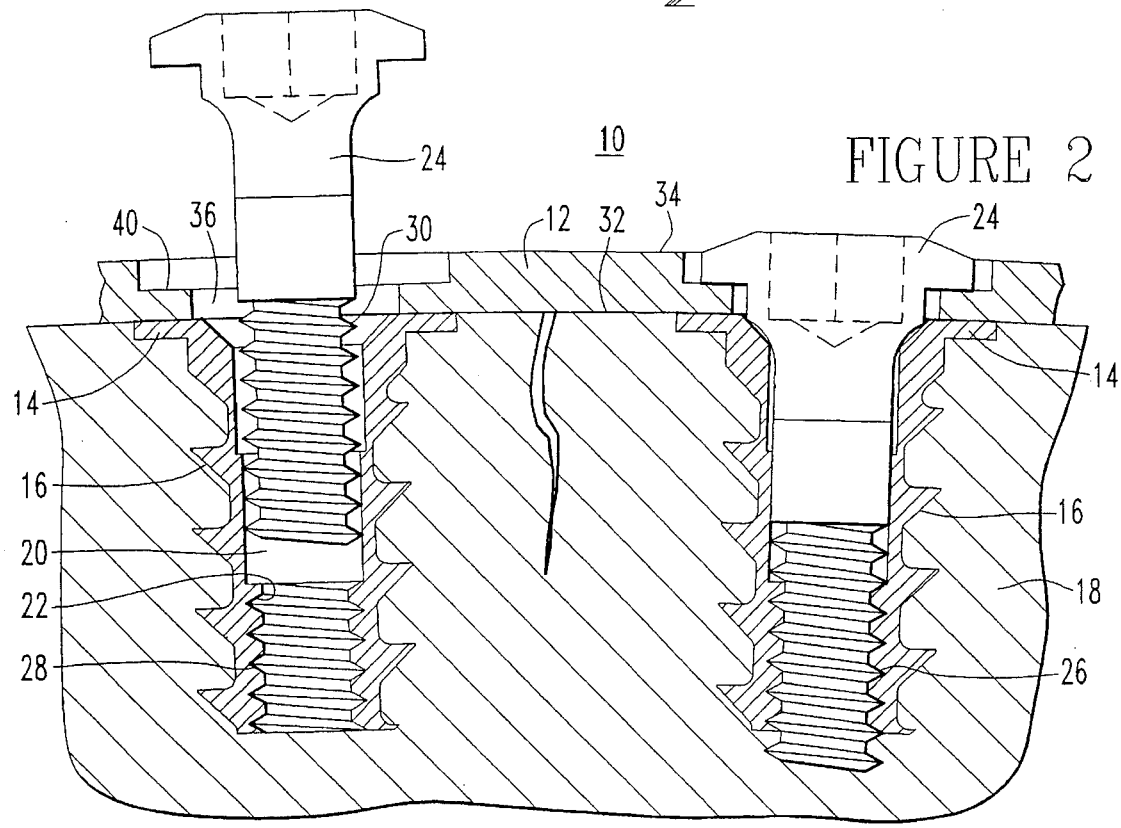

FIG. 1 is a top view of a device in which the present invention is embodied;

FIG. 2 is a cross-section view of the preferred embodiment of the device taken along line 2—2 of FIG. 1.

DESCRIPTION OF THE PREFERRED EMBODIMENTS

The present invention for an assembly for securing an element in place includes an anchor. The anchor has a hollow shank with an outer surface for engaging a bone and an interior surface. The assembly also includes a means for engaging the interior surface of the anchor for holding the element between the engaging means and the anchor. The anchor and engaging means have means for cooperating between one another to fix the engaging means to the anchor. For purposes of the preferred embodiment, the engaging means is a screw and the cooperating means are the mating threads of the interior of the anchor and the screw.

Reference will now be made in detail to the present preferred embodiments of the invention, examples of which are illustrated in the accompanying drawings. The exemplary embodiment of the assembly of the present invention is shown in FIGS. 1 and 2 and is designated generally by reference numeral 10.

As embodied herein and referring to FIGS. 1 and 2, the assembly 10 for securing an element 12 in place includes an anchor 14 having a hollow shank 20 with an outer surface 16 for engaging a bone 18 and an interior surface 22. The assembly further includes a screw 24 for engaging the interior surface 22 of the anchor 14 for holding the element 12 between the head of the screw 24 and the anchor 14. The screw 24 and the anchor 14 have mating threads 26 for cooperating to fixedly attach together.

Preferably, the anchor 14 has an outer surface 16 that is threaded to increase the pullout strength of the anchor 14 to bone 18 interface. While the preferred outer surface 16 of the anchor 14 is circular and threaded, it is contemplated as well within the scope of the present invention that a cross section of the bone contacting outer surface 16 of the anchor 14 can be any shape adaptable to insertion into a cavity in a bone. Additionally, an interfering projection for increasing the anchor pullout strength may be placed on the outer surface 16 of the anchor 14. Furthermore, the preferred anchor 14 has an interior surface 22 that is circular, and more preferably has threads 28.

The screw 24 has threads 30 for cooperating with the threaded interior surface 22 of the anchor 14. While the preferred engaging means is the screw 24, it is well contemplated within the scope of this invention that any fastening or engaging device possessing the required strength characteristics and adaptable to cooperative engagement with the interior surface 22 of the anchor 14 may be used to secure the element 12 in place. The preferred cooperating means are the threads 28 and 30 of the anchor 14 and screw 24, respectively.

The element 12 is preferably a plate having a contacting surface 32 for engaging the bone 18. Preferably, the contacting surface 32 curves to complement the bone 18. Additionally, the plate 12 has an opposite surface 34 opposite the contacting surface 32 and at least one opening 36 to receive the securing means or screw 24. The element 12, among many configurations that can bridge a fracture or strengthen a bone, can also be a rod having at least one hole through it for the screw 24.

The opening 36 in the element 12 goes through the contacting surface 32 to the opposite surface 34. The opening 36 in the plate 12 has a diameter preferably smaller than the flange of the anchor 14. The present invention allows for a smaller opening 36 in the element 12 to securely fix it to the surface of the bone, thereby providing the advantage of greater strength and structural integrity to the element 12. Note that the diameter of the outer surface 16 of the anchor 14 is not limited to the size of the opening 36 in the element 12. Preferably, the opening 36 is an elongated slot 38 for providing the element 12 adjustment along the major axis of the slot 38. The slot 38 preferably has a counterbore 40 for providing the element 12 adjustment along the minor axis of the slot 38. The counterbore 40 in the slot 38 provides adjustment by making the counterbore 40 larger across its diameter than the head of screw 24, while the diameter of the elongated portion of the screw 24 is less than the width of the opening 36. The relationship between the counterbore 40 and screw 24 is such that even if the screw 24 is shifted entirely to one side of the minor axis of the slot 38, the screw 24 cannot pass through the opening 36. The side walls of the opening 36 may be straight, countersunk or any other configuration for receiving the screw 24, however, it is preferable for the head of screw 24 to be substantially flush with the opposite surface 34 of the element 12.

Furthermore, a method for attaching a plate 12 having an opening 36 to opposite sides of a fracture in a bone 18 is disclosed. The steps comprise: forming a cavity in the bone 18 for receiving the anchor 14; fixing the anchor 14 having a hollow shank 20 with an outer surface 16 and an interior surface 22 into the cavity; placing the plate 12 against the bone 18 with the opening 36 in the plate 12 over the hollow shank 20 of the anchor 14; fixedly attaching the plate 12 by engaging the screw 24 into the hollow shank 20 of the anchor 14, whereby the plate 12 is held between the anchor 14 and the head of the screw 24. A preferred method of forming the cavity into the bone 18 is drilling, however any method of creating a cavity is contemplated within the scope of the present invention. The method may include the step of tapping the bone 18 before fixing the anchor 14.

Related art devices place an element against the bone first then secure it by installing a screw through openings in the structural element and into the bone. More recent plates attempt to improve attachment to the bone by using a connector assembly which is placed through the plate. Whereas, the present invention installs an anchor in the bone before the structural element is placed against the bone and then the screw is inserted.

Performance improvements made possible by the present invention are greater pullout strength at the bone-implant interface by virtue of the larger diameter and threads of the anchor, greater latitude in element placement without sacrificing assembly strength, and ease of removing the structural element without disturbing the bone-implant interface established by the anchor.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed herein, but that the invention include all embodiments falling within the scope of the appended claims.

We claim:

1. An assembly comprising:

an element having at least one opening for attachment to a bone;

an anchor having a hollow shank having an outer non-expansible threaded surface surrounding an interior surface, said interior surface of said hollow shank for extending into a cavity of the bone, said outer threaded surface for fixedly engaging the cavity of the bone; and an engaging member having a shank with an outer surface for insertion into said hollow shank to fixedly engage said outer surface of said engaging member to said interior surface of said hollow shank of said anchor for holding said element between said engaging member and said anchor, said engaging member and said anchor having means for cooperating to fix said engaging member to said anchor without expanding said outer irregular surface of said hollow shank.

2. The assembly of claim 1, wherein said interior surface is circular.

3. The assembly of claim 2, wherein said interior surface is threaded.

4. The assembly of claim 3, wherein said engaging member includes a screw having threads for cooperating with said interior surface of said hollow shank.

5. The assembly of claim 1, wherein said outer surface of said anchor has threads for engaging the cavity of the bone, the anchor having a proximal end for entering the cavity and an opposite distal end, said threads having an outer end facing toward said distal end of said anchor, said outer end being at approximately ninety degrees to a longitudinal axis through said hollow shank of said anchor.

6. The assembly of claim 1, wherein said outer surface of said anchor has threads for engaging the cavity of the bone, the anchor having a proximal end for entering the cavity and an opposite distal end, said threads having an inner end facing toward said proximal end of said anchor, said inner end being oblique with reference to a longitudinal axis through said hollow shank of said anchor.

7. An apparatus comprising in combination:

a plurality of anchors having a non-expansible outer threaded surface for fixedly engaging a cavity of a bone, each anchor having a hollow shank having an interior surface surrounded by said outer threaded surface, said interior surface of said hollow shank for extending into the cavity of the bone, each anchor having a length for substantial insertion into the bone;

an element for fixing to a bone surface; and means for securing said element to each anchor by fixedly engaging said interior surface of said hollow shank to hold said element between said securing means and each anchor without expanding said outer surface of said hollow shank.

8. The apparatus of claim 7, wherein said interior surface of each anchor is circular.

9. The apparatus of claim 8, wherein said securing means includes a screw for cooperating with said interior surface of each anchor.

10. The apparatus of claim 7, wherein said element includes a plate having a contacting surface for fixing to the bone, said contacting surface complementing the bone, said plate having an opposite surface opposite said contacting surface, and at least one opening through said plate from said contacting surface to said opposite surface, said opening to receive said securing means.

11. The apparatus of claim 10, wherein said opening in said plate includes an elongated slot for adjustment along a major axis of said slot and a counterbore in said slot for adjustment along a minor axis of said slot.

12. The apparatus of claim 10, wherein said outer surface of said anchor is larger than said opening in each plate.

13. An apparatus comprising in combination:

a first member having at least one opening for attachment to a bone;

an anchor having a hollow shank with a non-expansible threaded outer surface surrounding an interior irregular surface, said outer surface for attaching to walls of a cavity formed in the bone for fixing said anchor to the bone, said interior irregular surface of said hollow shank for extending into the cavity of the bone, said anchor having a length for substantial insertion into the bone; and a second member having an elongated portion for insertion through said opening of the first member and a head with a width larger than the width of said opening, said elongated portion having irregularities for cooperating with said interior irregular surface of said shank to fixedly attach said first member to said anchor without expanding said outer surface of said hollow shank.

14. A method for attaching an element having an opening to a bone, comprising the steps of:

providing an anchor having a hollow shank providing an interior surface surrounded by a non-expansible outer surface for fixedly engaging the bone, said interior surface of said hollow shank for extending into the bone;

forming a cavity in the bone for receiving the anchor;

fixing said non-expansible outer surface of said anchor into the cavity of the bone;

placing the element against the bone with the opening in the element over said hollow shank of said anchor; and fixedly attaching the element by engaging a holding member having a portion for insertion into said hollow shank of said anchor without expanding said outer surface of said hollow shank, whereby the element is held between said anchor and said holding member.

15. The method as recited in claim 14, further comprising tapping the bone before fixing said anchor.

16. The method as recited in claim 14, wherein the step of fixing includes threadably fixing said outer surface of said anchor into said cavity.

17. The method as recited in claim 14, wherein the step of providing includes threadably fixing said interior surface of said anchor into said cavity.

18. The method as recited in claim 17, wherein the step of fixedly attaching includes said holding member being a screw having threads for cooperating with said interior surface of said anchor to fix said screw to said anchor without expanding said outer surface of said hollow shank.

19. An assembly comprising:

an element having at least one opening for attachment to a bone;

an anchor having a hollow shank having a threaded outer surface surrounding a threaded interior surface, said interior surface of said hollow shank for extending into a cavity of the bone, said outer surface for fixedly engaging the cavity of the bone; and an engaging member having a shank with an outer surface for insertion into said hollow shank to fixedly engage said outer surface of said engaging member to said interior surface of said hollow shank of said anchor for holding said element between said engaging member and said anchor, said engaging member having means for cooperating to fix said engaging member to said interior surface of said hollow shank.

20. The assembly of claim 19, wherein said interior surface is circular.

21. The assembly of claim 19, wherein said cooperating means includes threads for cooperating with said interior surface of said hollow shank.

22. An apparatus comprising in combination:

a plurality of anchors having a threaded outer surface for fixedly engaging a cavity of a bone, each anchor having a hollow shank having a threaded interior surface surrounded by said outer surface, said interior surface of said hollow shank for extending into the cavity of the bone, each anchor having a length for substantial insertion into the bone;

an element for fixing to a bone surface; and means for securing said element to each anchor by fixedly engaging said interior surface of said hollow shank to hold said element between said securing means and each anchor.

23. The apparatus of claim 22, wherein said interior surface of each anchor is circular.

24. The apparatus of claim 22, wherein said securing means includes a screw for cooperating with said interior surface of at least one anchor.

25. The apparatus of claim 22, wherein said element includes a plate having a contacting surface for fixing to the bone, said contacting surface having a curve to compliment the bone, said plate having an opposite surface opposite said contacting surface, and at least one opening through said plate from said contacting surface to said opposite surface, said opening to receive said securing means.

26. The apparatus of claim 25, wherein said outer surface of each anchor is larger than said opening in said plate.

27. An apparatus comprising in combination:

a first member having at least one opening for attachment to a bone;

an anchor having a hollow shank having a threaded outer surface surrounding a threaded interior surface, said outer surface for attaching to walls of a cavity formed in the bone for fixing said anchor to the bone, said threaded interior surface of said hollow shank for extending into the cavity of the bone, said anchor having a length for substantial insertion into the bone; and a second member having an elongated portion for insertion through said opening of the first member and a head with a width larger than the width of said opening, said elongated portion having irregularities for cooperating with said threaded interior surface of said shank to fixedly attach said first member to said anchor.

28. A method for attaching an element having an opening to a bone, comprising the steps of:

providing an anchor having a hollow shank with a threaded interior surface surrounded by a threaded outer surface for fixedly engaging the bone, said threaded interior surface of said hollow shank for extending into the bone;

forming a cavity in the bone for receiving the anchor;

fixing said threaded outer surface of said anchor into the cavity of the bone by rotating said anchor;

placing the element against the bone with the opening in the element over said hollow shank of said anchor; and fixedly attaching the element by engaging a screw having a threaded portion for cooperating with said threaded interior surface of said hollow shank, whereby the element is held between said anchor and said holding member.

29. The method as recited in claim 28, further comprising tapping the bone before fixing said anchor.

* * * * *